(12) United States Patent
Cavallaro et al.

(10) Patent No.: US 6,918,306 B1
(45) Date of Patent: Jul. 19, 2005

(54) ADJUSTABLE FLEXURE LOADING APPARATUS FOR TESTING LONG SPAN BEAMS

(75) Inventors: Paul V. Cavallaro, Raynham, MA (US); Daniel Perez, Jr., Middletown, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 55 days.

(21) Appl. No.: 10/657,774

(22) Filed: Sep. 8, 2003

(51) Int. Cl.[7] ............................. G01N 3/20; G01N 3/02
(52) U.S. Cl. .......................................... 73/849; 73/856
(58) Field of Search ....................... 73/849, 852, 856, 73/853, 855

(56) References Cited

U.S. PATENT DOCUMENTS

| | | | |
|---|---|---|---|
| 3,898,873 A | 8/1975 | Glassmeyer | |
| 4,488,444 A * | 12/1984 | Weidmann et al. | .... 73/862.452 |
| 4,594,900 A | 6/1986 | Pellerin et al. | |
| 4,789,947 A | 12/1988 | Maciejczak | |
| 4,911,004 A * | 3/1990 | Leon | ........................... 73/168 |
| 5,345,826 A | 9/1994 | Strong | |
| 5,386,442 A | 1/1995 | Diaz et al. | |
| 5,448,918 A | 9/1995 | Tucchio | |
| 5,699,274 A | 12/1997 | Starostovic | |
| 5,913,246 A | 6/1999 | Simonelli et al. | |
| 6,042,315 A | 3/2000 | Miller et al. | |
| 6,053,052 A | 4/2000 | Starostovic | |
| 6,079,247 A * | 6/2000 | Gravier | ....................... 72/175 |
| 6,216,531 B1 | 4/2001 | Zhou | |
| 6,263,636 B1 | 7/2001 | Corston | |

* cited by examiner

Primary Examiner—Edward Lefkowitz
Assistant Examiner—Lilybett Martir
(74) Attorney, Agent, or Firm—James M. Kasischke; Michael P. Stanley; Jean-Paul A. Nasser

(57) ABSTRACT

An adjustable loading apparatus for supporting a long span beam in a flexure test by a load application device is disclosed. The apparatus includes an upper support structure including an elongated support beam, at least one support bracket adjustably mountable along a longitudinal span thereof, and a saddle member selectively pivotally mounted in the at least one upper support bracket for engaging with a specimen under test. The upper support structure is positioned normal to the load application device and a lower support structure is positioned parallel and co-planar to the upper support structure. The lower support structure includes an elongated support beam, at least one spacing member adjustably mounted along a longitudinal span thereof, a lower support bracket adjustably mounted along a longitudinal span of the spacing member, and a saddle member selectively pivotally mounted in the lower support bracket for engaging with a specimen under test.

13 Claims, 2 Drawing Sheets

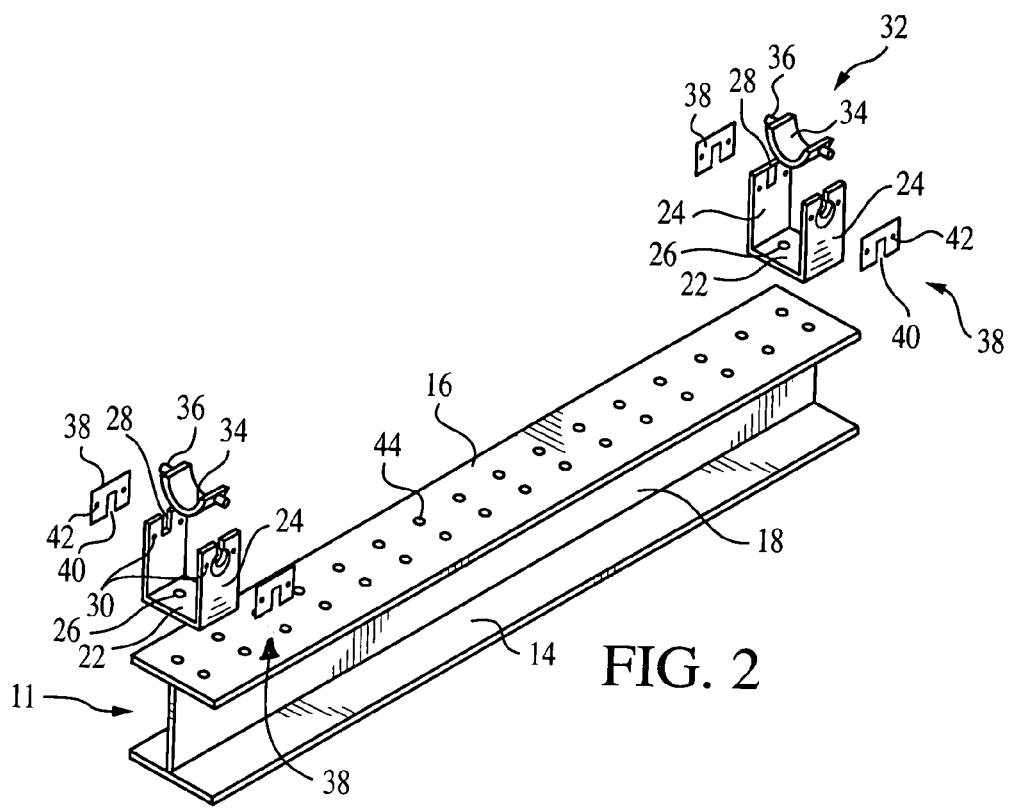
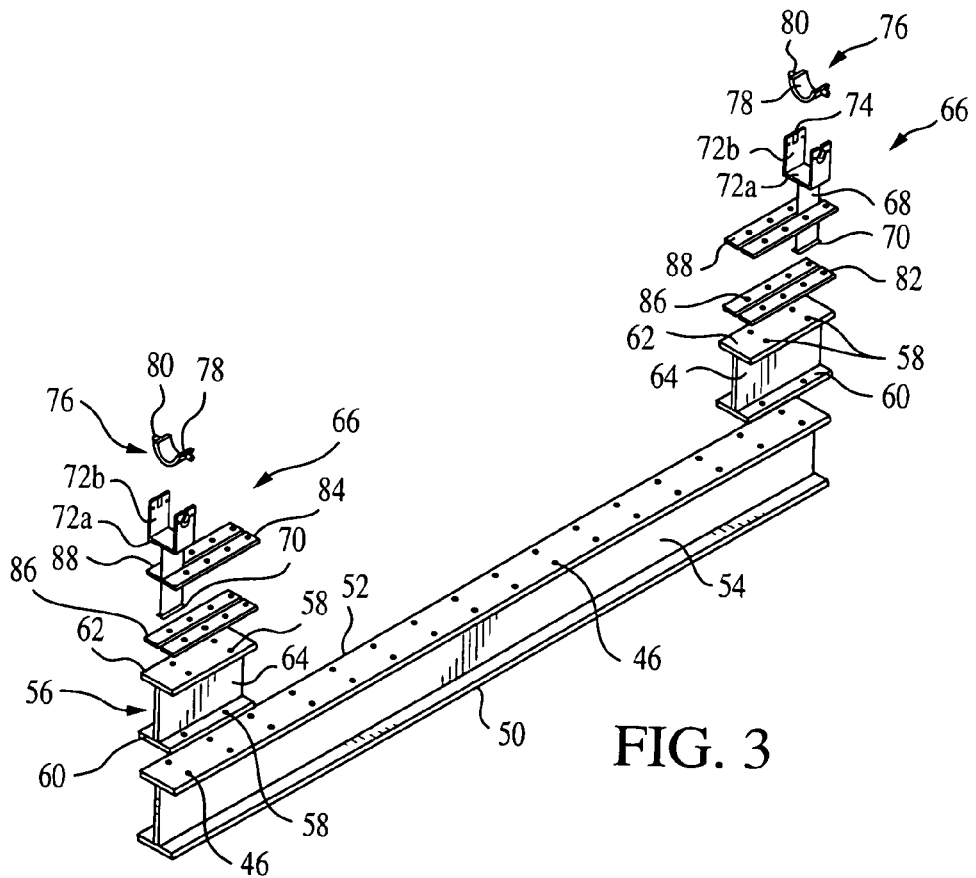

ADJUSTABLE FLEXURE LOADING APPARATUS FOR TESTING LONG SPAN BEAMS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

This invention generally relates to an apparatus for flexure testing long, slender shapes.

More particularly, the invention relates to an apparatus for flexure testing long, slender shapes such as solid or hollow structural beams, tubes, pipes, cylinders, and the like in which a length of the specimen under test is not limited and the orientation of the specimens is not limited by a position of load columns on a load application device.

(2) Description of the Prior Art

The current art for flexure testing limit the specimen length to an inside distance between load columns of a load application device and require specimens to be oriented within the plane defined by the load columns.

The following patents, for example, disclose flexure testing, but do not disclose flexure testing in which a specimen is aligned perpendicularly to the load column plane such that no restriction is imposed on specimen length.

Specifically, Glassmeyer (U.S. Pat. No. 3,898,873) discloses an intermodel cargo container bottom lift tested by means of a test fixture including adjustable supports which are connected to the lower corner fittings to maintain the container in a raised position free of a supporting surface. The upper corner fittings are first connected to a suitable hoisting device and upon lifting are placed in tension. The lower corner fitting lifting capability of the container is then tested by releasing the tension in the cables, the bottom lift test fixtures being placed in compression.

Hayashi (U.S. Pat. No. 4,590,900) discloses a valve supporting arrangement of an internal combustion engine. The upper retainer is for retaining an upper portion of a valve spring shaped like a perforated spinning top and is axially dividable into two identical elements which are coaxially disposed about the upper portion of the valve stem when assuming its operative condition. The retainer has, when assuming the operative position, a configuration which comprises a collar portion which is sized to be coaxially disposed within an upper portion of the valve spring, an annular flange portion extending radially outward from the upper end of the collar portion and engaging with the upper end of the valve spring, and means for achieving a spline connection between the central portion of the retainer and the upper portion of the valve stem.

Maciejczak (U.S. Pat. No. 4,789,947) discloses, in conjunction with an unmanned, remotely controllable apparatus for inspecting, testing and viewing and for examination and evaluation of the general condition, state of repair, and of the quality of fabrication of mechanical structures including bridges, an assembly including a guide track carried by a space frame fastened to extend transversely of a bridge or other structure at an underside thereof. The track supports a carrier adapted for transporting, viewing, examining, treating and testing apparatus for controlled movement and manipulation of the apparatus along a path delineated by the guide track. In a preferred embodiment of the invention the carrier supports one or more turntables and one or more articulated arms and linked arm assemblies at remote ends of which selectable viewing and testing devices are attachable. The space frame itself may be moved lineally along the bridge, on an underside thereof so that through the combination of the transversely moving carrier and the lineally movable space frame, an entire aerial zone may be traversed.

Strong (U.S. Pat. No. 5,345,826) discloses a static load tester that provides tensile testing of plated test specimens to detect hydrogen embrittlement damage from plating processes. The functional components of the device are centrally aligned within a channel of an I-beam frame. A load cell and electronic readout provide the user with a measure of the tensile force applied to up to eight test specimens mounted end to end in a tester. Tension is applied to the specimens through use of a simple threaded rod and nut load application system at the base of the device. A static load tester may be incorporated into each channel of the I-beam frame, thereby providing a double testing unit. Additionally, a series of I-beam frame tester configurations may be incorporated into one multiple testing unit. Each multiple testing unit has a number of static load testers equal to double the number of I-beam frames mounted into the unit. The tension applied to any individual tester in a multiple testing unit may be displayed on a single electronic readout through use of a switch box coupled between the individual testers and the readout.

Diaz et al. (U.S. Pat. No. 5,386,442) discloses an apparatus and a method for measuring and controlling the crack growth rate within a double cantilever beam type test specimen. The arms of the test specimen are fitted with a pressure-actuated bellows to induce a predetermined load and with a sensing assembly to provide feedback on the amount of beam displacement resulting from the application of that load. In this manner, a loaded test specimen may be remotely mounted and adjusted inside the reactor pressure vessel or piping of a nuclear reactor in order to maintain a stress intensity which is constant or which varies in a predetermined manner for inducing stress corrosion cracking or corrosion fatigue in the specimen.

Tucchio (U.S. Pat. No. 5,448,918) discloses a biaxial compression testing device formed by two modified beams joined together to form an X-shape with the support structure, such as webs and upper flanges, removed in the region of the X intersection, thereby leaving a rectangular opening. The rectangular opening has dimensions slightly greater than the widths of the beams and is open from the upper surfaces downward to the lower surfaces which are joined together forming an X-configuration. This configuration has a flexing characteristic in the direction perpendicular to the plane of the joined beams. A test specimen support plate is attached to the underside of one of the upper surfaces and is located so as to slide below the opposing upper surface during flexing of the X-beam assembly. Each beam is supported by a roller pin. Additional roller pins are located on the specimen support plate between each beam upper flange and a specimen to be tested. The single actuating force is applied to cause the X-beams to flex into a concave shape thereby applying a part of the actuating force axially along each beam. The configuration provides a force transfer assembly which is actuated by a single load force, but provides a biaxial load to the test specimen.

Starostovic, Jr. (U.S. Pat. No. 5,699,274) discloses a performance testing system, i.e., performance of a material under a load concentrated in a single area. The system is computerized and automatically applies a load to a panel to be tested, reads and records deflection of the panel without operator involvement, and provides a printed test report.

Simonelli et al. (U.S. Pat. No. 5,913,246) discloses a machine for the cyclic load testing in tension, compression, torsion, shear, or any combination thereof of any one of a number of different sizes, types and configurations of test specimens at a fixed or adjustable predetermined load and cycle rate and comprising a machine frame in which is mounted a drive shaft, any number of intermediate shafts as required, and a camshaft or crankshaft. At the workstation of the machine, appropriate fixtures and tooling are either fixed, rotating, or in motion, as required to conduct the particular test to be performed. When the test specimen is to be in motion, the motion may be derived from a driving source separate from the primary mover or camshaft, for instance, but not limited to an independent motor or cylinder. This source of motion may also be taken through a drive train or any suitable means from the same driving source as the camshaft or from the camshaft itself or from any other moving member in the system. A motion is ultimately imparted to drive the test specimen bolder, thereby setting the test specimen in motion.

Miller et al. (U.S. Pat. No. 6,042,315) discloses a fastener body comprising a head and a shank fabricated from a composite material. The head has at least one side which extends beyond the side of the shank and has two other sides coplanar with the shank. A fastener for engaging a liner has perpendicular lengthwise and widthwise reference axes and a head and a shank, with the shank extending in a first lengthwise direction away from the head, the head further having at least one extension that extends in the widthwise direction beyond the shank for engaging the liner, wherein substantially all lengthwise directed load components transmitted from the liner to the head are transmitted through the extension.

Starostovic (U.S. Pat. No. 5,699,274) discloses a performance testing system for woodbased panels. The testing includes performance of a material under a load concentrated in a single area, performance of edge support systems under a concentrated load and performance of a material under static bending conditions. The system is computerized and automatically applies a load to a panel to be tested, reads and records deflection of the panel without operator involvement, and provides a printed test report.

Zhou (U.S. Pat. No. 6,216,531) discloses an adapter for use in the testing of shear strength of an adhesive as applied to a test specimen. The adapter has a structure that permits it to be used on testing machines either in a tension or in a compression mode. The adapter as a testing tool includes a pair of coacting force blocks which slidably engage each other and move relative to each other. Each such force block has a central opening into which a test specimen may be inserted. The openings in each of the force blocks engage a different one of the two test coupons that make up a testing specimen. The force blocks further have bearing surfaces that oppose each other so that they may engage the like opposing ends of the test specimen.

It should be understood that the present invention would in fact enhance the functionality of the above patents by providing an adjustable apparatus for supporting long span beams in a flexure testing machine regardless of their length or orientation.

SUMMARY OF THE INVENTION

Accordingly, it is a general purpose and primary object of this invention to provide an adjustable apparatus for supporting long span beams.

It is a further object of this invention to provide an adjustable apparatus for supporting long span beams in a flexure testing machine.

It is a still further object of this invention to provide an adjustable apparatus for supporting a long span beam specimen in an orientation normal to that of the operating structure on a load application device.

It is a still further object of the invention to provide an adjustable apparatus for supporting a long span beam specimen that is simple to operate and easily implemented into existing load testing devices.

To obtain the objects described, there is disclosed an adjustable apparatus for supporting a long span beam specimen in a flexure test by a load application device. The apparatus includes an upper support structure including an elongated support beam, at least one support bracket adjustably mountable along a longitudinal span thereof, and a saddle member selectively pivotally mounted in the at least one upper support bracket for engaging with a specimen under test. The upper support structure is positioned normal to the load application device and a lower support structure is positioned parallel and co-planar to the upper support structure. The lower support structure includes an elongated support beam, at least one spacing member adjustably mounted along a longitudinal span thereof, a lower support bracket adjustably mounted along a longitudinal span of the spacing member, and a saddle member selectively pivotally mounted in the lower support bracket for engaging with a specimen under test.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 2 is an exploded bottom perspective view of a top fixture of the specimen supporting apparatus shown in FIG. 1; and FIG. 3 is an exploded top perspective view of a bottom fixture of the specimen supporting apparatus shown in FIG. 1.

DESCRIPTION OF THE PREFERRED EMBODIMENT

Figure 1:
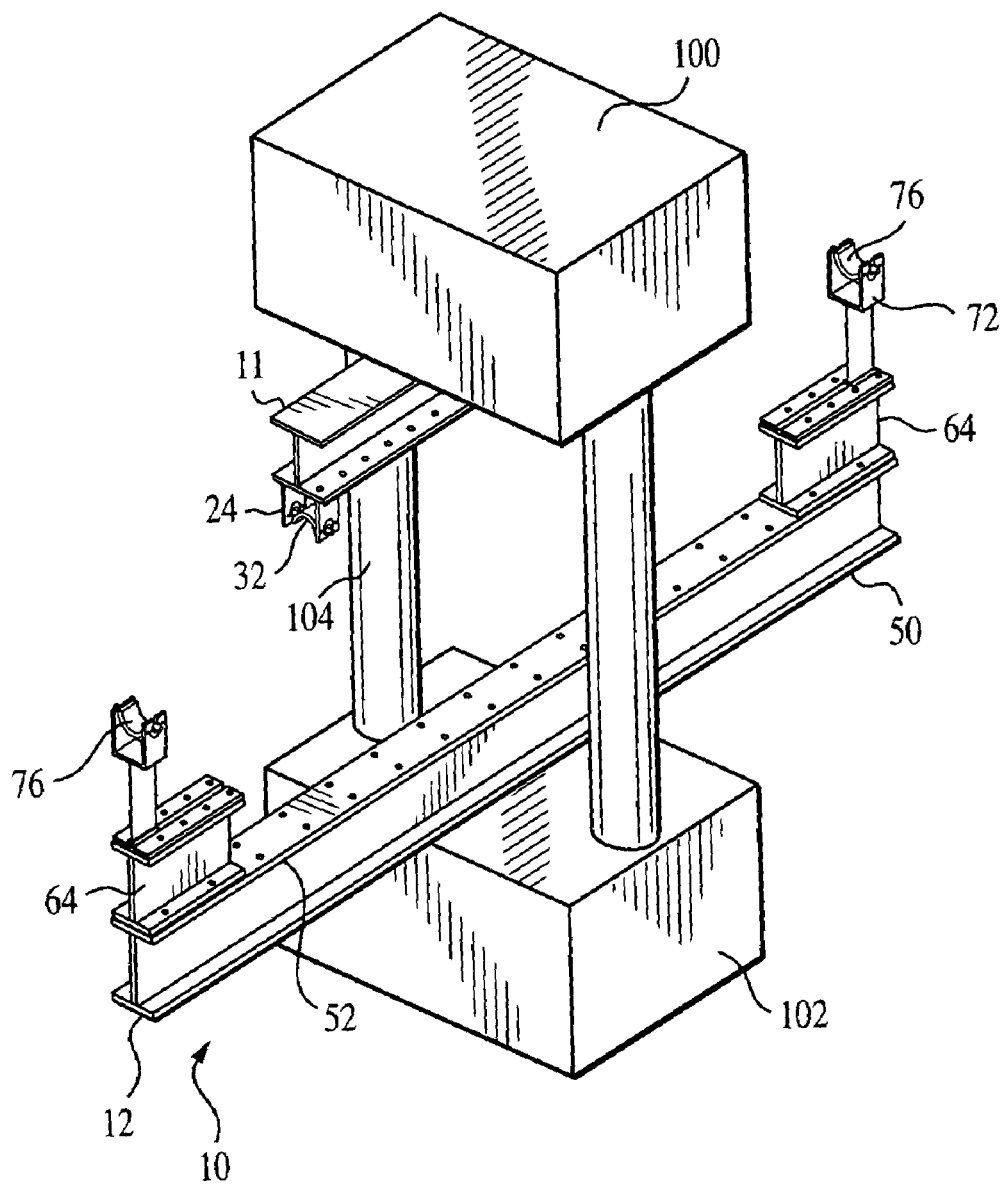
FIG. 1 is a perspective view of a specimen supporting apparatus in a characteristic flexure testing environment according to a preferred embodiment of the present invention.

In general, the present invention is directed to a specimen supporting apparatus generally intended for use in flexure testing of long slender shapes (such as, but not limited to, solid or hollow structural beams, tubes, pipes, cylinders, and the like) in which the load-deflection or stress-strain characteristics of a specimen being tested are sought.

Referring first to FIG. 1, there is shown a perspective view of a specimen supporting apparatus 10 according to the present invention and in a working environment of a typical flexure testing device.

The specimen supporting apparatus 10 includes an upper support structure 11 and a lower support structure 12. These upper and lower support structures, 11, 12, are each formed in a basic I-beam shape. For the purposes of the present design shown, these upper 11 and lower 12 support structures are formed of aluminum 6061-T6 W6x25 I-beams, however, other materials known to those skilled in the art may be used.

Referring still to FIG. 1, it can be seen that the upper and lower support structures 11, 12 are positioned parallel to and co-planar with each other. The upper support structure 11 is shown mounted transverse to a moving upper platen 100 of the testing device and the lower support structure 12 is shown mounted transverse to a lower stationary platen 102 of the testing device. The upper platen 100 is spaced from the lower platen 102 by a pair of hydraulically operated columns 104 as is known in the art such that the upper platen 100 is adjustably positioned with a testing force relative to the lower platen 102. Operation of the testing device is omitted for the sake of brevity and as having no part of the subject invention other than explanation of a suggested environmental use of the specimen supporting apparatus 10 being described.

Additional details of the upper support structure 11 and the lower support structure 12 of the specimen support device 10 are shown in each of FIGS. 2 and 3, respectively and are intended to be referenced in connection with FIG. 1 and the following description.

The upper support structure 11 is shown in FIG. 2 in an inverted and exploded perspective view in order to better understand the parts thereof. Specifically, the upper support structure 11 is shown in an I-beam shape with opposing end plates 14, 16 and an inner wall 18 perpendicular to and spacing apart the end plates 14, 16, thus defining the "I" shape of the structure. A plurality of paired and spaced apertures 44 are formed through one of the end plates 16 along an entire length thereof.

At least one support bracket 20 is mounted to the apertured end plate 16. The support bracket 20 includes a base portion 22 for surface contact with the apertured end plate 16 and side walls 24 projecting from opposing sides of the base portion 22 and away from the fixture 10. The base portion 22 of the support bracket 20 has apertures 26 formed therein which are aligned to mate with corresponding apertures 44 formed in the end plate 16 of the upper support structure 11. The connection of the support bracket 20 to the end plate 16 is with suitable fixing means such as screws, bolts, or the like.

Each of the projecting side walls 24 of the support bracket 20 include a centered slot 28 at the distal end thereof and a pair of apertures 30, one to each side of the centered slot 28. A saddle member 32 includes a saddle portion 34 and opposing pins 36 extending from outer ends of the saddle portion 34 such that the pins 36 seat into the centered slots 28 of the support bracket 20 with the saddle portion 34 fit between the side walls 24 and enabling pivotal rotation of the saddle member 32 with respect to the support bracket 20. Each pin 36 is secured in the centered slots 28 with a slotted fixing plate 38. The slotted fixing plate 38 is rectangular and includes a slot 40 formed in an edge thereof with an aperture 42 on each side of the slot 40. The slot 40 slides over the pin 36 of the saddle member 32 and the apertures 42 align with the apertures 30 of the side walls 24 for securement by any suitable means such as a screw, welding or the like. This securement enables movement of the saddle member 32 without separation from the support bracket 20.

Still referring to the upper support structure 11, if a single support bracket 20 is utilized, then it is positioned at the mid span of the upper support structure 11. This arrangement enables a three-point flexure loading in connection with the lower support structure 12.

If two support brackets 20 are utilized, then each support bracket 20 is equidistantly positioned to each other from a mid-point of the upper support structure 11 according to the matching paired aperture patterns 44 between the upper support structure 11 and the support brackets 20. This arrangement enables a four-point flexure loading in connection with the lower support structure 12. The upper support bracket 20, in whatever number utilized, is attached to the apertured end plate 16 of the upper support structure 11 with bolts or other suitable fastening means (not specifically shown for simplicity). It should be understood, however, that these support brackets 20 are movable along the length of the upper support structure 11 and should therefore be fixed with secure, yet removable means.

Referring now to details of the lower support structure 12, the lower support structure 12 is also shown in an I-beam shape with opposing end plates 50, 52 and an inner wall 54 perpendicular to and spacing apart the end plates 50, 52, thus defining the "I" shape of the structure. A plurality of paired and spaced apertures 46 are formed through one of the end plates 52 along an entire length thereof. These paired and spaced apertures 46 are in the end plate 52 which faces the similarly formed apertures 44 of the upper support structure 11.

At least one offset member 56 is provided in connection with the lower support structure 12. This offset member 56 is bolted to the lower support structure 12 using a paired aperture pattern 58 that matches the spacing of the paired apertures 46 in the end plate 52 of the lower structure 12. The offset member 56 provides an offset clearance between a specimen under test and the lower support structure 12 such that the specimen under flexure loads will not deflect to the point where contact between the specimen and lower support structure 12 is made.

The offset member 56 is structurally similar in shape to the lower support structure 12 in that it is of an I-beam shape. The I-beam shape of the offset member 56 includes opposing end plates 60, 62, each having paired aperture patterns 58, and an inner wall 64 perpendicular to and spacing apart the end plates 60, 62. The offset member 56 is substantially shorter than the lower support structure 12, spanning only approximately three sets of paired apertures 46 thereon.

A slider 66 is adjustably positioned with respect to the offset member 56. The slider 66 includes a support leg 68 with a T-shaped base 70 and a support bracket 72 at an end opposing the T-shaped base 70. The support bracket 72 includes a base portion 72a integrally connected to the support leg 68 and side walls 72b projecting from opposing sides of the base portion 72a and away from the offset member 56.

Each of the projecting side walls 72b of the support bracket 72 include a centered slot 74 at the distal end thereof. A saddle member 76 is seated in the support bracket 72 and includes a saddle portion 78 and opposing pins 80 extending from outer ends of the saddle portion 78 such that the pins 80 seat into the centered slots 74 of the support bracket 72 with the saddle portion between the side walls 72b and enabling pivotal rotation of the saddle member 76 with respect to the support bracket 72. Unlike the saddle member 32 of the upper support bracket 20, the pins 80 of the saddle member 76 in the lower support bracket 72 need not be secured in the centered slots 74. This is because the weight of the specimen to be tested will secure the saddle member 76 without separation from the support bracket 72.

A series of spacers 82 and overlying fixing plates 84 are attached to that end wall 62 of the offset member 56 which is not secured to the apertured end wall 52 of the lower support fixture 12. The spacers 82 and fixing plates 84 create a slide positioning mechanism securing the T-shaped base 70 of the slider 66 to the offset member 56 through paired apertures 86, 88 of the spacers and fixing plates, respectively. These apertures 86, 88 align with corresponding apertures 58 of the spacer 56. This provides a finer spacing control for adjustments less than the pitch distance between the matching paired apertures 58 in the offset member 56 and those apertures 46 in the lower support structure 12.

Due to the arrangement of spacers 82 and overlying fixing plates 84, there are two different ways to adjust the distance between saddles 76 mounted at opposite ends of the lower support structure 12.

In a first distance adjustment, a coarse adjustment can be made according to the selection of the bolt hole groups 26 used to secure the upper brackets 20 to the upper support structure 11 and, likewise, the paired apertures 58 used to secure the offset members 56 to the lower support structure 12.

In a second distance adjustment, a finer adjustment mechanism is included in between the offset member 56 and the slider 66. The series of spacers 82 and fixing plates 84 clamp the slider 66 to the offset member 56. This provides spacing control that is less than the pitch distance between the matching aperture patterns 58 in the offset member 56 and the paired apertures 46 in the lower support structure 12.

During operation and as shown in FIG. 1, the lower support structure 12 and the attached components as described are positioned normal to the load column plane of the columns 104 of the flexure testing device and centered on the stationary platen 102 (assumed to be the bottom platen) of the flexure testing device. It is desired that equal lengths of the end plates 50, 52 of the lower support structure 12 overhang the front and rear sides of the plane defined by the load columns 104. Similarly, the upper support structure 11 and attached components are positioned normal to the load column plane and centered on the moving platen 100 (assumed to be the top platen) of the flexure testing device. The upper and lower support structures 11, 12 are checked to be co-planar to each other and the complete assembly is checked to be normal to the load column plane.

The specimen is secured in the saddles 76 of the lower support structure 12 and the testing device applies the load by moving the upper support structure 11 downward such that the upper saddles 32 are pushing down on the specimen under test and the lower saddles 76 react the load upwards. The saddles 32, 76 will rotate as the specimen deforms. This is the follower-loading mode.

To utilize the non-follower-loading mode, locking pins (not shown) are placed through corresponding holes in the side walls 72b of the slider 66 and the pins 80 of the saddles 76. The same is done for the apertures 30 in the side walls 24 of the upper bracket 20 and the pins 36 of the saddles 32.

It should be understood that the subject specimen supporting apparatus 10 is known to accommodate 96 inches long specimens, however, there is no restriction for obtaining specimen lengths beyond 96 inches. Both coarse and fine adjustment mechanisms are included for setting the spans between load and support points. A full range of load and support point positions is thereby provided.

A rotational locking mechanism such as a pin is included in the saddle design to enable the user to test in either follower or non-follower loading modes. In a follower-loading mode, the saddles rotate as the specimen deforms since the resulting force vector remains in the same direction relative to the localized region of the specimen to which it is applied as the specimen deforms globally. In a non-follower loading mode, the force vector remains in the same global direction at all times and does not change directions as the specimen deforms. The non-follower mode will transfer the load from the saddle outer edge rather than along the saddle surface are. Accordingly, to operate in a non-follower monde, locking pins (not specifically shown) are inserted through corresponding holes in the sides of the bottom slider and the axles of the lower saddles, thereby securing them against rotation. The same is done for the holes in the sides of the top support and the axles of the upper saddles.

Other additional benefits are realized when coupling the specimen supporting apparatus 10 to a flexure testing device. These include, but are not limited to, testing the specimen in a load-controlled mode such as a constant loading rate of 10 pounds per minute; and testing the specimen in a displacement-controlled mode such as a constant displacement rate of 1.0 inch per minute. These types of tests are known in the art and are included as examples of the uses of the present invention.

There are several contemplated singular or combined alternatives to the described subject disclosure, and these are intended to be included within the scope of the invention, although the invention is not limited to these suggested alternatives.

In a first alternative, a T-shaped slotted block could be used as an alternative to the slide positioning mechanism of spacers 82 and fixing plates 84.

In a second alternative, the saddles 32 may be installed within the upper bracket 20 and the saddle 76 may be installed at the bottom sliders using bearings, needles, rollers, or the like to reduce rotational friction forces when using the follower loading mode.

Alternative structural shapes may be used for the various components, such as box beam shapes for the upper and lower support structures 11, 12 rather than I-beam shapes.

The slide positioning mechanism of spacers 82 and fixing plates 84 shown in connection with the lower support structure 12 may also be implemented in connection with the upper support structure 11.

In view of the above detailed description, it is anticipated that the invention herein will have far reaching applications other than those of flexure testing of elongated materials.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed is:

1. An adjustable apparatus for supporting a long span specimen in a flexure test by a load application device, said apparatus comprising:

an upper structure including an I-shaped elongated beam, at least one support bracket adjustably mountable along a longitudinal span thereof, and a saddle pivotally mounted in said at least one upper support bracket, said saddle engageable in support of the specimen and said upper structure engageable with the load application device opposite said saddle wherein said upper structure includes a plurality of spaced and paired apertures formed as pairs in at least one end plate bordering an inner plate of said I-shaped elongated beam such that one aperture in each pair is on an opposite side of said inner plate; and a lower structure spaced apart from said upper structure, said lower support structure including a support beam, at least one spacing member adjustably mounted along a longitudinal span thereof, a lower support bracket adjustably mounted along a longitudinal span of said spacing member, and a saddle pivotally mounted in said lower support bracket to face said upper support structure and engageable with the specimen.

2. The apparatus according to claim 1 wherein said upper support bracket includes a plurality of spaced and paired apertures at a base portion of said upper support bracket, said apertures of said upper support bracket alignable with said apertures of said end plate and;

said upper support bracket further including a receiving slot formed on opposing side walls of said bracket for supporting said saddle.

3. The apparatus according to claim 2 wherein said saddle includes a pin protruding from opposite sides of said saddle, each pin pivotal in a corresponding receiving slot of said side walls.

4. The apparatus according to claim 3 further comprising a securing plate mountable on each side wall of said upper support bracket, said securing plate securing said pins within said receiving slots.

5. An adjustable apparatus for supporting a long span specimen in a flexure test by a load application device, said apparatus comprising:

an upper structure including an elongated beam, at least one support bracket adjustably mountable along a longitudinal span thereof, and a saddle pivotally mounted in said at least one upper support bracket, said saddle engageable in support of the specimen and said upper structure engageable with the load application device opposite said saddle; and a lower structure spaced apart from said upper structure, said lower support structure including a I-shaped support beam, at least one spacing member adjustably mounted along a longitudinal span thereof, a lower support bracket adjustably mounted along a longitudinal span of said spacing member, and a saddle pivotally mounted in said lower support bracket to face said upper support structure and engageable with the specimen wherein said lower structure includes a plurality of spaced and paired apertures formed as pairs in at least one end plate bordering an inner plate of said I-shaped support beam such that one aperture in each pair is on an opposite side of said inner plate.

6. The apparatus according to claim 5 wherein said lower support bracket further comprises a slider as a base portion center mounted at a distal end of a leg portion, and a pair of side walls projecting from opposite sides of said base portion, each side wall of said slider including a receiving slot formed therein for supporting said saddle of said lower structure.

7. The apparatus according to claim 6 wherein said saddle of said lower structure includes a pin protruding from opposite sides of said saddle, each pin pivotable in a corresponding receiving slot of said side walls.

8. The apparatus according to claim 7 wherein said lower structure further includes a spacer member normal to said longitudinal span of said lower structure and including a first portion of said spacer adjustably secured to the apertured surface of said lower structure and a second portion opposite the first portion adjustably supporting said leg of said slider.

9. The apparatus according to claim 8 wherein said lower support bracket is slidably adjustable relative to said spacer and said spacer is slidably adjustable relative to said lower structure.

10. The apparatus according to claim 8 further comprising a plate mechanism mechanically attachable to said spacer and interposing extending protrusions of said leg portion therebetween.

11. The apparatus according to claim 10 wherein said lower support bracket is slidably adjustable relative to said spacer and said spacer is slidably adjustable relative to said lower structure.

12. The apparatus according to claim 10 wherein said plate mechanism includes a spacer plate superposed by a fixing plate, said spacer plate being mounted directly on the opposite surface of said spacer.

13. An adjustable apparatus for supporting a long span specimen in a flexure test by a load application device, said apparatus comprising:

an upper structure including an elongated beam, at least one support bracket adjustably mountable along a longitudinal span thereof, and a saddle pivotally mounted in said at least one upper support bracket, said saddle engageable in support of the specimen and said upper structure engageable with the load application device opposite said saddle; and a lower structure spaced apart from said upper structure, said lower support structure including a support beam, at least one spacing member adjustably mounted along a longitudinal span thereof, a lower support bracket adjustably mounted along a longitudinal span of said spacing member, and a saddle pivotally mounted in said lower support bracket to face said upper support structure and engageable with the specimen;

said upper structure including a plurality of spaced and paired apertures formed as pairs in at least one end plate bordering an inner plate of said I-shape of said upper structure such that one aperture in each pair is on an opposite side of the inner plate;

said upper support bracket further comprises a slider as a base portion center mounted at a distal end of a leg portion, and a pair of side walls projecting from opposite sides of said base portion, each side wall of said slider including a receiving slot formed therein for supporting said saddle of said upper structure.

* * * * *